US007906624B2

(12) United States Patent
Greene et al.

(10) Patent No.: US 7,906,624 B2
(45) Date of Patent: Mar. 15, 2011

(54) BINDING PEPTIDOMIMETICS AND USES OF THE SAME (75) Inventors: Mark I. Greene, Penn Valley, PA (US); Ramachandran Murali, Swarthmore, PA (US); Hongtao Zhang, Devon, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 587 days.

(21) Appl. No.: 10/589,688

(22) PCT Filed: Feb. 18, 2005

(86) PCT No.: PCT/US2005/005383
§ 371 (c)(1),
(2), (4) Date: Apr. 16, 2008

(87) PCT Pub. No.: WO2005/081898
PCT Pub. Date: Sep. 9, 2005

(65) Prior Publication Data
US 2008/0206136 A1  Aug. 28, 2008

Related U.S. Application Data (60) Provisional application No. 60/546,224, filed on Feb. 20, 2004.

(51) Int. Cl.
C12N 15/09 (2006.01)
A61K 38/00 (2006.01)
(52) U.S. Cl. .................... 530/387.3; 530/808; 435/69.1; 435/440; 435/7.6
(58) Field of Classification Search .......................... None
See application file for complete search history.

(56) References Cited

U.S. PATENT DOCUMENTS

| 5,328,985 A | 7/1994 | Sano et al. |
| 5,334,702 A | 8/1994 | Greene et al. |
| 5,663,144 A | 9/1997 | Greene et al. |
| 5,665,539 A | 9/1997 | Sano et al. |
| 5,919,764 A | 7/1999 | Greene et al. |
| 5,922,553 A | 7/1999 | Eberwine et al. |
| 6,022,523 A | 2/2000 | Degrado et al. |
| 6,100,377 A | 8/2000 | Greene et al. |
| 6,391,590 B1 | 5/2002 | Sano et al. |
| 6,413,934 B1 | 7/2002 | Stayton et al. |
| 6,451,995 B1 | 9/2002 | Cheung et al. |
| 6,497,881 B1 | 12/2002 | Meruelo et al. |
| 6,743,592 B1 | 6/2004 | Greene et al. |
| 7,045,286 B2 | 5/2006 | Greene et al. |
| 7,144,991 B2 | 12/2006 | Goshorn et al. |
| 2002/0094534 A1 | 7/2002 | Greene et al. |
| 2003/0148932 A1* | 8/2003 | Greene et al. ............ 514/9 |

FOREIGN PATENT DOCUMENTS

| WO | WO 9933965 A1 * | 7/1999 |
| WO | WO 02/066980 A1 | 8/2002 |
| WO | WO 02066980 A1 * | 8/2002 |

OTHER PUBLICATIONS

Murali, R. et al., "Antibody like peptidomimetics as large scale immunodetection prodes," Cellular and Molecular Biology, Mar. 2003, 49(2), 209-216.
Berezov, A. et al., "Disabling ErbB Receptors with Rationally Designed Exocyclic Mimetics of Antibodies: Structure-Function Analysis," J. Med. Chem., 2001, 44, 2565-2574.
Park, B-W, et al., "Rationally designed anti-HER2/neu peptide mimetic disables P185 (HER2/neu lyrosine kinases in vitro and in vivo," Nature Biotechnology, Feb. 2000, 18, 194-198.
Argarana, et al., "Molecular cloning and nucleotide sequence of the streptavidin gene," Nucleic Acids Res. (1986), 14 (4): 1871-1882.
Chirinos-Rojas, C.L. et al., "A peptidomimetic antagonist of TNF-alpha-mediated cytotoxicity identified from a phage-displayed random peptide library," J Immunol. (1998), 161(10):5621-6.
Dubel, S. et al., "Bifunctional and multimeric complexes of streptavidin fused to single chain antibodies (scFv).," J Immunol Methods (1995), 178(2):201-9.
Felix, A.M., "Applications of BOP reagent in solid phase synthesis", Int. J. Pep. Prot. Res. 1988 31:231-238.
Giralt, E. and Andrea eds, In Peptides, ESCOM, Leiden, The Netherlands 1991,131-133.
Hruby, "Conformational restrictions of biologically active peptides via amino acid side chain groups," Life Sci. (1982)31: 189-199.
Karp, et al., "Identification of biotinylated molecules using a baculovirus-expressed luciferase-streptavidin fusion protein," Biotechniques (1996), 20 (3):452-456, 458-459.
Kipriyanov, et al., "Affinity enhancement of a recombinant antibody: formation of complexes with multiple valency by a single-chain Fv fragment-core streptavidin fusion," Protein Eng. (1996), 9 (2): 203-211.
Krpriyanov, et al., "Single-chain antibody streptavidin fusions: tetrameric bifunctional scFv-complexes with biotin binding activity and enhanced affinity to antigen," Hum. Antibodies Hybridomas (1995), 6 (3): 93-101. Kishore et al., "A recombinant homotrimer, composed of the alpha helical neck region of human surfactant protein D and C1q B chain globular domain, is an inhibitor of the classical complement pathway," J. Immunol (2001) 166: 559-565.
Koo, et al., "Development of a streptavidin-conjugated single-chain antibody that binds Bacillus cereus spores," Applied Environ. Microbiol. (1998), 64(7): 2497-2502.
Le, et al., "A streptavidin-cellulose-binding domain fusion protein that binds biotinylated proteins to cellulose," Enzyme Microb. Technol. 16 (6): 496-500,1994.
Lee, W. et al., "Solution structure of the tetrameric minimum transforming domain of p53," Nature Struct. Biol. (1994),1:877-890.

(Continued)

Primary Examiner — Anand U Desai
Assistant Examiner — Samuel Liu
(74) Attorney, Agent, or Firm — Woodcock Washburn, LLP (57) ABSTRACT A multimeric peptidomimetic that comprises two or more monomers is disclosed. The monomers comprise an exocyclic peptide comprising a ring structure, a flexible linker sequence and a multimeric motif. Use of the monomers, a nucleic acid molecule encoding monomers, recombinant expression vectors comprising the nucleic acid molecule and host cells comprising a recombinant expression vector are disclosed. Methods of delivering a drug, a toxin, a nucleic acid molecule, a radionuclide or a detectable compound to a cell are disclosed.

1 Claim, 6 Drawing Sheets

OTHER PUBLICATIONS

Murali et al.,"Structure-based design of immunologically active therapeutic peptides," *Immunol. Res.* (1998) 17: 163-169.

Ohno and Meruelo, "Multi-drug delivery system using streptavidin-transforming growth factor—alpha chimeric protein," *DNA Cell Biol.* (1996), 15 (5): 401-406.

Ohno, et al., "Cell-specific, multidrug delivery system using streptavidin-protein A fusion protein," *Biochem. Mol. Med.* (1996)58 (2): 227-233.

Pearce, et al. "Linear gene fusions of antibody fragments with streptavidin can be linked to biotin labelled secondary molecules to form bispecific reagents," *Biochem. Mol. Biol. Int.* (1997)42 (6): 1179-1188.

Ploux, 0. et al., "Cyclization of peptides on a solid support. Application to cyclic analogs of substance P,"*Int. J. Pep. Prot. Res.* (1987), 29: 162-169.

Porstmann, T. et al., "Enzyme immunoassay techniques. An overview," *J Immunol Methods.* (1992), 150(1-2):5-21.

Porstmann, B. et al., "Which of the commonly used marker enzymes gives the best results in colorimetric and fluorimetric enzyme immunoassays: horseradish peroxidase, alkaline phosphatase or beta-galactosidase?" *J Immunol Methods* (1985), 79(1):27-37.

Prasad et al., "Contrasting solution conformations of peptides containing alpha,alpha-dialkylated residues with linear and cyclic side chains," *Biopolymers* (1995) 35: 11-20.

Rogers et al., "Characterization of disulfide crosslink formation of human vimentin at the dimer, tetramer, and intermediate filament levels," *J Struct Biol.* Jul.-Aug. 1996; 117 (1) : 55-69.

Roland J, et al., "The synthetic CD4 exocyclic CDR3.AME(82-89) inhibits NF-kappaB nuclear translocation, HIV-1 promoter activation, and viral gene expression," *DNA Cell Biol.*, Nov. 1999 18(11):819-28.

Romani, S. et al., "Synthesis of the trypsin fragment 10-25/75-88 of mouse nerve growth factor. II. The unsymmetrical double chain cystine peptide," *Int. J. Pep. Prot. Res.* (1987), 29: 107-117).

Sano and Cantor, "Expression of a cloned streptavidin gene in *Escherichia coli*," *Proc. Natl. Acad. Sci. USA* (1990), 87 (1) : 142-146.

Sano and Cantor, "A streptavidin-protein A chimera that allows one-step production of a variety of specific antibody conjugates," *Biotechnology* (1991), 1378-1381.

Sano and Cantor, "Expression vectors for streptavidin-containing chimeric proteins,"*Biochem. Biophys. Res. Commun* (1991), 176 (2): 571-577.

Sano et al., "A streptavidin-metallothionein chimera that allows specific labeling of biological materials with many different heavy metal ions," *Proc. Natl. Acad. Sci. USA* (1998), 89 (5): 1534-1538.

Saragovi et al., "Design and synthesis of a mimetic from an antibody complementarity-determining region," *Science* (1991), 253: 792-795.

Schiller et al., "Synthesis of side-chain to side-chain cyclized petide analogs on solid supports," *Int. J. Pep. Prot. Res.* (1985), 25: 171-177.

Schweitzer et al., "Inaugural article: immunoassays with rolling circle DNA amplification: a versatile platform for ultrasensitive antigen detection," *Proc Natl Acad Sci U S A.* (2000), 97(18):10113-9.

Sheppard, R. C., "Acid-labile resin linkage agents for use in solid phase peptide synthesis ," *Int. J. Peptide Res.* (1982), 20: 451-454.

Srinivasan, M. et al., "Immunomodulatory peptides from IgSF proteins: a review," *Curr Protein Pept Sci.* (2005), 6(2):185-96.

Tannous et al., "T7 RNA polymerase as a self-replicating label for antigen quantification," *Nucleic Acids Res* (2002), 30(24):e140.

Walsh and Swaisgood, "An *Escherichia coli* plasmid vector system for production of streptavidin fusion proteins: Expression and bioselective adsorption of streptavidin-β-galactosidase," *Biotech. Bioeng.* (1994)44: 1348-1354.

Williams et al.,"Development of biologically active peptides based on antibody structure," *Proc. Natl Acad. Sci. USA* (1989), 86: 5537-5541.

Zhang X. et al., "Synthetic CD4 exocyclics inhibit binding of human immunodeficiency virus type 1 envelope to CD4 and virus replication in T lymphocytes," *Nat Biotechnol.* (1997), 15(2):150-4.

Zhang et al., "Crystal structure of recombinant human platelet factor 4," *Biochem* (1994), V33: 8361-8366.

Zhang et al., "New perspectives on anti-HER2/neu therapeutics", Drug news and Perspectives, Aug. 2000, 13(6), 325-329.

\* cited by examiner

BINDING PEPTIDOMIMETICS AND USES OF THE SAME

CROSS-REFERENCE TO RELATED APPLICATIONS

This application is a national stage application of PCT International Application PCT/US2005/005383, filed Feb. 18, 2005, which claims priority to U.S Provisional Patent Application 60/546,224, filed Feb. 20, 2004.

FIELD OF THE INVENTION

The present invention relates to peptidomimetics that can be used in detection assays, as therapeutics and as substitutes for monoclonal antibodies in other applications.

BACKGROUND OF THE INVENTION

This application claims priority to U.S. Provisional Application Ser. No. 60/546,224, filed Feb. 20, 2004, which is incorporated herein by reference.

Monoclonal antibody (mAb) technology and the various uses of such proteins with specific binding activity are well known. For example, mAbs are used as therapeutics, imaging agents, diagnostic reagents and affinity substrates.

Streptavidin is a protein very closely related to a protein avidin which provides a very stable noncovalent complex with vitamin D-biotin. Avidin itself is a very highly specialized protein that is only rarely expressed. Streptavidin, on the other hand, is readily expressed in a species *Streptomyces*, in *Streptomyces avidinii*. Streptavidin specifically binds a water soluble vitamin D-biotin (vitamin H). Similarly to avidin, it also binds rapidly and almost irreversibly and with a remarkably high, affinity to any molecule which contains an unhindered biotin. Streptavidin, contrary to avidin, is carbohydrate free and thus more suitable, for example, for X-ray crystallographic studies because of its homogenous molecular structure, or for various other detection techniques because of reduced non-specific binding.

The streptavidin gene has been cloned and expressed in *E. coli* (Sano and Cantor, Proc. Natl. Acad. Sci. USA 87(1):142-146, 1990; Agarana, et al., Nucleic Acids Res. 14(4):1871-1882, 1986). Fusion constructs of streptavidin, and truncated forms thereof, with various proteins, including single-chain antibodies, have also been expressed in *E. coli* (Sano and Cantor, Biotechnology (NY) 9(12):1378-1381, 1991; Sano and Cantor, Biochem. Biophys. Res. Commun. 176(2):571-577, 1991; Sano, et al., Proc. Natl. Acad. Sci. USA 89(5):1534-1538, 1992; Walsh and Swaisgood, Biotech. Bioeng. 44:1348-1354, 1994; Le, et al., Enzyme Microb. Technol. 16(6):496-500, 1994; Dubel, et al., J. Immunol. Methods 178(2):201-209, 1995; Kipriyanov, et al., Hum. Antibodies Hybridomas 6(3):93-101, 1995; Kipriyanov, et al., Protein Eng. 9(2):203-211, 1996; Ohno, et al., Biochem. fol. Med. 58(2):227-233, 1996; Ohno and Meruelo, DNA Cell Biol. 15(5):401-406, 1996; Pearce, et al. Biochem. Mol. Biol. Int. 42(6):1179-1188, 1997; Koo, et al., Applied Environ. Microbiol. 64(7):2497-2502, 1998) and in other organisms (Karp, et al., Biotechniques 20(3):452-459, 1996).

U.S. Pat. No. 5,328,985 describes streptavidin-protein A chimeric proteins. Protein A (Sp A) is a cell wall constituent of *Staphylococcus aureus*. Protein A has been shown to specifically interacts with immunoglobulins, mainly IgG from mammalian species. The most essential feature of the protein of U.S. Pat. No. 5,328,985 is the ability of binding to biotin and IgG. In the current invention, the tetramer contains a cell-binding domain as well as biotin-binding streptavidin. In a preferred embodiment the cell-binding domain consists of CDR peptide of antibodies that bind to cell surface receptors.

U.S. Pat. No. 6,391,590 concerns streptavidin-metallothionein chimeric proteins. Metallothionein protein is able to bind a variety of heavy metals with high variety. The most essential feature of the protein of U.S. Pat. No. 6,391,590 is the ability of binding to both biotin and heavy metal metals.

U.S. Pat. No. 6,413,934 concerns streptavidin mutants having secondary functional domain. In this patent, the second functional domain is inserted into streptavidin sequence. In the current invention, the cell-binding domain is separated, but linked to streptavidin via a linker sequence.

U.S. Pat. No. 6,451,995 concerns single chain FV (scFv) polynucleotide or peptide constructs of anti-ganglioside $G_{D2}$ antibodies. This patent also describes a method of connect this scFv to streptavidin or a pro-drug converting enzyme. Gangliosides are acidic glycosphingolipids found on the outer surface of most cell membranes. In many tumors there is abnormal glycolipid composition and structure. Disialoganglioside $G_{D2}$ has been found in a wide spectrum of human tumors, including neuroblastoma, osteosarcomas and other soft tissue sarcomas, medulloblastomas, high grade astrocytomas, melanomas, and small cell lung cancer. In the current invention, cell-binding domains binds to receptors (protein) on the cell surface.

U.S. Pat. No. 6,497,881 concerns a streptavidin-protein A chimeric protein that can be used as a delivery system to form a non-covalent complex of a toxin or nucleic acid and an antibody. In the current invention, the tetramer can be used as a therapeutic reagent for cancers without coupling to addition toxin or nucleic acid or antibody.

U.S. Patent Application 20030095977 concerns a streptavidin and scFV fusion. In this particular application, antibody and antigen-binding fragment were also claimed for the second component in the fusion protein. Antibody fragment refers to "fragments, derived from or related to an antibody, which bind antigen and which in some embodiments may be derivatized to exhibit structural features that facilitate clearance and uptake, e.g., by the incorporation of galactose residues. This includes, e.g., F(ab), F(ab)'$_2$, scFv, light chain variable region ($V_L$), heavy chain variable region ($V_H$), and combinations thereof." U.S. patent application 20030095977 does not teach using a short amino acid sequence (5-8 amino acid residues) derived from a single CDR unit of the antibody.

SUMMARY OF THE INVENTION

The present invention relates to multimeric peptidomimetics that comprise two or more monomers. The monomers comprise an exocyclic peptide comprising a ring structure, a flexible linker sequence and a multimeric motif.

The present invention further relates to nucleic acid molecule encoding such monomers, recombinant expression vector comprising such nucleic acid molecules, and host cells comprising such recombinant expression vectors.

The present invention also relates to methods of delivering a drug, a toxin, a nucleic acid molecule, a radionuclide or a detectable compound to a cell. The methods comprise the step of contacting the cell with a multimeric peptidomimetic that comprises two or more monomers. The monomers comprise: an exocyclic peptide comprising a ring structure, a flexible linker sequence and a multimeric motif. The cell expresses a protein which binds to an amino acid sequence present in the exocyclic peptide of a monomer of: the multimeric protein.

The present invention further relates to the use of a monomer that comprises an exocyclic peptide comprising a ring structure, a flexible linker sequence and a multimeric motif to produce a multimeric peptidomimetic.

The present invention also relates to a purified recombinant protein having a cell binding domain and a biotin-binding streptavidin core sequence. The cell binding domain comprises an active domain of a heterologous polypeptide and is fused to the N-terminus of streptavidin molecule by a flexible linker.

The present invention also relates to tetrameric protein complexes comprising such proteins.

DETAILED DESCRIPTION OF THE INVENTION

A binding peptidomimetic (BIP) is an exocyclic peptide containing a small protein construct designed to replace an antibody and further including a motif which facilitates formation of multimers. The BIP contains three distinct parts: 1) a small loop of exocyclic peptide mimics (ePm) which contain about 5-20 amino acid residues, preferably 5-12 amino acid residues, 2) a flexible linker that allows proper disposition of the exocyclic mimetics for protein binding without interference by the multimerization motif comprising 4-20 amino acid residues, preferably 5-12 amino acid residues, and 3) a small protein motif which functions in the formation of multimer complexes and non-covalent bonding to other molecules.

The BIPs of the present invention provide useful and convenient constructs to produce detectable binding molecules such as those useful in detection, quantification and profiling assays. Additionally, the BIPs of the invention provide a convenient means to produce multimeric forms of small biologically active constrained peptides that provide improved activity over monomeric forms, thereby approaching the activity of monoclonal antibodies.

The CDR technology is well known and has been described in U.S. Pat. No. 5,334,702, U.S. Pat. No. 5,663,144, and U.S. Pat. No. 5,919,764, which are incorporated herein by reference. Antibody molecules bind to their antigens via six variable loops called Complementary Determining Regions (CDRs). The CDR3 from heavy chain often mediates that specificity. A general methodology for design of constrained cyclic CDR mimetics is described by Williams et al. (Proc. Natl Acad. Sci. USA 1989 86:5537-5541), Sargovi et al. (Science 1991 253:792-795) and Murali et al. (Immunol. Res. 1998 17:163-169). In general, CDRs comprise a 6 to 15 mer peptide constrained to be cyclic and modified by aromatic residues. CDR mimetics are small molecules (about 1 kDa) which are capable of mimicking their parent antibodies in terms of specificity, affinity and biological activity. Cyclic forms of CDR mimetics contain approximately 5 to 13 constrained amino acids.

An important step in the design of CDRs and CDR mimetics for use in the present invention is the delineation of the residues that are important for activity. This is generally accomplished by first synthesizing a set of analogs from the bioactive domain of the original antibody or receptor or ligand of different lengths and establishing the minimal chain lengths for the complete and partial activities. Once the minimal chain length has been established, each side chain can be systematically varied to determine the importance of charge, steric bulk, hydrophobicity, aromaticity, and chirality at each position. After evaluation of the properties of a large set of analogs, it is possible to identify the functional groups and conformation features involved in binding. Different conformationally constrained analogs can then be developed. Various means for constraining peptides have been developed.

One means involves introducing a conformationally constrained amino acid. Hruby (Life Sci. 1982 31:189-199) describes the synthesis of a large number of amino acid and dipeptide derivatives with built-in conformational constraints, as well as their incorporation into biologically active peptides. Prasad et al. (Biopolymers 1995 35:11-20) also describes a method of constraining the conformation of an amino acid unit by replacing the hydrogen atom at the α-carbon with a methyl group to produce a dialkylamino acid. U.S. Pat. No. 6,022,523, which is incorporated herein by reference describes a method that restricts the conformational freedom of amino acids by introducing a double-bond at the C-α and C-β atoms.

Another means for constraining peptides involves introduction of covalent cross-links. Constraining the peptide backbone by introduction of covalent cross-links provides more dramatic effects than incorporating unusual amino acids. Macrocyclization is often accomplished by forming an amide bond between the peptide N- and C-termini, between a side chain and the N or C terminus, or between two side chains. A head-to-tail cyclization of side protected peptides synthesized by Fmoc/t-butyl solid phase procedures on polysterine resin derivatized with 4-hydroxymethyl-3-methoxyphenoacetic acid, the first generation dialkoxy-benzyl linkage agent, has been described by Sheppard, R. C. (Int. J. Peptide Res. 1982 20:451-454). In addition, the analogous linkage agent, 4-(4-hydroxymethyl-3-methoxyphenoxy)-butyric acid (HAMA), was recently employed in fragment condensation and solid phase synthesis of peptides with these highly acid sensitive linkers (In Peptides, E. Giralt and D. Andreu eds, ESCOM, Leiden, The Netherlands 1991, 131-133). The enkephalin analogs described by Schiller provide an example of side-chain to backbone covalent cyclization in which covalent attachment of the e-amino group of the D-lys residue to the C terminal backbone carboxylate group of Leu produces a cyclic 16-membered ring analog with high potency and significant μ receptor selectivity (Schiller et al. Int. J. Pep. Prot. Res. 1985; 25:171-177). Benzotriazole-1-yl-oxy-tris-(dimethylamino)-phosphonium hexafluorophosphate (BOP-reagent) and carboimide/1-hydroxy-benzotriazole combinations have also been reported to be useful in the formation of cyclic peptides (Felix, A.M. Int. J. Pep. Prot. Res. 1988 31:231-238). Degrado et al. have also developed a biologically active cyclized peptide analog of the GP IIb/IIIa complex using m-aminomethylbenzoic acid as the linker (U.S. Pat. No. 6,022,523). Prot. Res. 1985; 25:171-177). BOP-reagent and carboimide/1-hydroxy-benzotriazole combinations have also been reported to be useful in the formation of cyclic peptides (Felix, A. M. Int. J. Pep. Prot. Res. 1988 31:231-238). Degrado et al. have also developed a biologically active cyclized peptide analog of the GP IIb/IIIa complex using m-aminomethylbenzoic acid as the linker (U.S. Pat. No. 6,022,523).

Disulphides can also be formed by oxidation via introduction of cysteine at certain positions. For example, Romani, S. (Int. J. Pep. Prot. Res. 1987 29:107-117) demonstrated that non-symmetrical disulphides can be built with the help of the di-tertbutyl aster of azodicarboxylic acid. Ploux, 0. (Int. J. Pep. Prot. Res. 1987 29:162-169) also describes a method for formation of non-symmetrical disulphides via thiol displacement of the 3S-3-nitro-2-pyridinesulfenyl group.

U.S. Pat. No. 6,100,377, which is incorporated herein by reference describes how to make and use aromatically modified exocyclic peptides. The peptides described therein contain a cyclic portion that includes an sequence modeled on a CDR sequence which functions in the way the CDR functions and exocyclic sequences which include the N and C termini of the protein. The molecule is cyclicized by an internal bond between residues other than both of the terminal residues. The residues, which are not part of the cyclic portion, are referred to as exocyclic portions or sequences. In U.S. Pat. No. 6,100, 377 at least one exocyclic sequence comprises an aromatic amino acid residue.

According to the present invention, exocyclic peptides are provided which comprise exocyclic portions that include a flexible linker and a multimerizing or linking motif. The exocyclic peptides of the invention may include aromatic amino acid residues at one or two exocylcic sequences. The ring portion is formed by disulfide bonds between at least one non-terminal residue and another peptide residue that may or may not be a non-terminal residue. The amino acids within the ring define the binding pharmocophores while the exocyclic residues mimic the framework region of an antibody (i.e.

supports conformation of the loop and provides the framework for exocyclic construct) and contain a flexible linker and multimerizing or linking motif. The flexible linker is generally 4-20 amino acid residues. In some embodiments, it is 4, 5, 6, 7, 8, 9, 10, or 11 amino acid residues. In some embodiments, it is 12, 13, 14, 15, 16, 17, 18, 19 or 20 amino acid residues.

Examples of multimerizing or linking motifs include streptavidin, vimenin and similar trimerizing or tetramerizing motifs. In some embodiments, the tetramerizing motifs is a leucine zipper motif, a human platelet factor motif, a Human Superoxide dismutase motif, or a p53 tetramerizing domain. In some embodiments, the multimerizing or linking motifs include streptavidin or multimerizing fragments thereof. Preferably, or multimerizing fragments of streptavidin retain their biotin binding capability. In some embodiments, the multimerizing or linking motifs includes P53 tumor suppressor or fragments thereof which comprise multimerizing motifs (Lee, W. et al. (1994) Nature Struct. Biol. 1, 877-890, which is incorporated herein by reference). In some embodiments, the multimerizing or linking motifs includes Human platelet factor or fragments-thereof which comprise multimerizing motifs (Zhang et al., Biochem (1994) V33, pp: 8361-6, which is incorporated herein by reference). In some embodiments, the multimerizing or linking motifs includes the trimerizing neck region of surfactant protein D with the globular head region of C1q B chain as a fusion to *Escherichia coli* maltose binding protein (Kishore et al., J. Immunol. 166:559-565, 2001, which is incorporated herein by reference). In some embodiments, the multimerizing or linking motifs includes vimentin or multimerizing fragments thereof (Rogers et al., J Struct Biol. 1996 July-August; 117(1):55-69, which is incorporated herein by reference.) These protein motifs are used to connect two or more cyclic peptides to produce prepare multimeric forms of the cyclic peptide thereby producing a more active peptide. Alternatively, the small protein motif is used to non-covalently link the exocyclic peptide to a detection probe.

In some embodiments, the sequence of ring portion of the exocyclic peptides of the invention corresponds to the variable region of an antibody. A short peptide from an antibody, receptor or ligand can be engineered into the ring portion of an exocyclic peptide to construct a BIP that mimics the binding activity of the antibody, receptor or ligand from which it was modeled while having only one hundredth the mass. Compared to establishing a diverse repertoire of antibodies, a diverse repertoire of BIPs can be generated relatively easily using phage display libraries that contain randomized loop regions, a flexible linker and a linking or multimerizing motif. The phage library thus can produce a library of BIPs that can be panned to identify BIPs with loop regions that bind to the target molecule, such as an antigen, ligand or receptor. Alternatively, BIPs may be created synthetically with or without organic chemical modifications. In some embodiments, the sequence of ring portion of the exocyclic peptides of the invention corresponds to the variable region of an antibody that binds to a protein used as a cancer marker, therapeutics target or imaging target such as Her2, EGFR, VEGF, CEA, PSA, HER3, HER4, CD-20, TNF-α, IL-1, TNFR, FAS, RANKL/TRANCE, OPG, CD40, CD28, CD3, CD4, IL-4 and IL-13.

In some embodiments, the sequence of ring portion of the exocyclic peptides of the invention corresponds to the regions of a receptor or other protein involved in protein binding. Such regions retain their ability to bind to their ligand.

BIPs can be fused with other domains at either the N- or C-terminus. Detector BIPs (dBIP) have a tail domain linked to the exocyclic peptide to attach the exocyclic peptide to a solid support such as a microplate or chip. Amplification BIPs (aBIP) have a domain that includes an amplifiable template linked to the exocyclic peptide.

Since BIPs contain a multimerization or linking domain, the can be used to prepare multimeric forms of exocyclic peptides (mBIP). Monomeric forms of the exocyclic peptide have limited affinity and there is difficulty in improving affinity through modifications. By providing higher order forms of the BIP through multimerization, affinities of the molecules may approach those of monoclonal antibodies. Accordingly, mBIPs can replace monoclonal antibodies in therapeutic and diagnostic applications.

BIPs can be used in detection and quantification assays such as immuno-PCR, immuno-rolling circle amplification (immuno-RCA), immuno-aRNA as well as any other assay that employs antibodies. Similarly, BIPs can be used in drug screening assays to identify compounds that enhance or inhibit protein-protein interactions known to have biological significance. Two proteins can be contacted with each other in the absence or presence of a test compound. BIPs can be used to determine whether the protein-protein interaction is enhanced or disrupted.

BIPs can also be used to map protein-protein interactions. For example fluorescently labeled or stained BIPs which are highly specific to proteins can be used to determine the site on a protein involved in protein-protein interaction, thus indicating a drug target.

Using diverse display techniques a number of BIPs can be identified which bind to the same site on a target molecule. A comparison of the different BIPs provides insight into the scaffold and functional groups involved in the interaction with the epitope. This information can be used in the development of small drugs with properly positioned functional groups or pharmocophores.

For successful translation from peptide to drug-like: molecule, two important conditions must be met: 1) conformational flexibility in the constrained peptide and 2) estimation in the appropriate scaffold and size.

Diversity displays followed by competitive binding assays offer unique ways to sample pharmacophores via different side chain groups simultaneously. A set of pharmacophores obtained from a group of competitively binding constrained BIPs is used to translate the peptide binding surface into a small drug like molecule. The translation is achieved by combination of computational database search (e.g. distance geometry constraint) and by biochemical/biological (e.g. complement binding epitope) analysis. Unconstrained peptides containing more than 7-8 amino acids cannot be used in this approach.

The translation of binding BIPs to drug leads involves the following basic steps. First, the exocyclic peptide offer an approximate ring size which defines the boundary of the scaffold dimension. A chemical database search is used to select different types of scaffolds amenable for synthesis as well as fit within allowed boundaries. Second, a set of pharmacophores identified from the group of peptides that compete with each other for binding are analyzed for consensus, cross correlation (e.g. neutral polar change at one position may have been compensated by a polar charged functional group in the phage), relative orientation in the three dimensional space and binding complementarity (as antibody mirror binding epitope to target protein). Finally, the third step is to identify this (potential drug like molecules) from a fast search (via distance and conformational constraints) of chemical-databases such as MDL, ACD or Maybridge chemical libraries. Hits validated by biochemical/biological assay can be improved either by combinatorial chemistry or other conventional means.

The invention relates to a method of improving the affinity and function of cell targeting peptides by engineering a tetrameric structure to such peptides. In one embodiment, such a tetramer binds to the target cells with higher affinity, and further inhibits the growth of target cells by depriving the vitamin Biotin from being utilized by target cells. In an alternative embodiment, the tetramer can be linked to a biotinylated compound such as a drug, toxin, nucleic acid, radionuclide or other detectable agent. The tetramer carries the drug, toxin, nucleic acid, radionuclide or other detectable agent to targeted cells. The nucleic acid can be for example DNA or RNA and it can be a biotinylated single stranded nucleic acid bound to the biotin binding site of the tetramer protein. In an alternative embodiment, the nucleic acid can be a duplex nucleic acid that forms a complementary triplex with a biotinylated single stranded nucleic acid, which is in turn bound to the biotin binding site.

Examples of chemotherapeutics include common cytotoxic or cytostatic drugs such as for example: methotrexate (amethopterin), doxorubicin (adrimycin), daunorubicin, cytosinarabinoside, etoposide, 5-fluorouracil, melphalan, chlorambucil, and cis-platin.

Examples of toxins include but are not limited to: ricin, ricin A chain (ricin toxin), *Pseudomonas* exotoxin (PE), diphtheria toxin (DT), *Clostridium perfringens* phospholipase C (PLC); bovine pancreatic ribonuclease (BPR), pokeweed antiviral protein (PAP), abrin, abrin A chain (abrin toxin), cobra venom factor (CVF), gelonin (GEL), saporin (SAP), modeccin, viscumin and volkensin The chimeric proteins designed and expressed according to the current invention are molecules contain the Biotin-binding property of streptavidin and the specific cellular target-binding property attributed to the peptide binding domain. Properties of both sub-domains, combined, provide a new recombinant tetrameric derivative which possesses full biotin-binding ability, which binds one or more cellular target per tetramer, and which are able to deprive biotin from being utilized by the target cells. The capacity of biotin binding of the tetramer can be used to carry biotinylated molecules to target cells.

The method of the invention relates to the steps of forming a complex between a streptavidin-protein A fusion protein; an antibody, that is specific for a cell surface protein, which undergoes endocytosis after binding with the antibody; and some targeted material e.g. a biotinylated multidrug resistance (mdr) gene product, prodrug, toxin or nucleic acid; isolating the complex from toxin that is not bound to the biotin binding site; and exposing the target cell, to the complex so that the targeted material enters the cell.

One aspect of the current invention is a recombinant streptavidin-Protein A chimeric protein having two independent biological recognition specificities. Another aspect of the current invention is an expression system for the cloned streptavidin gene which expresses streptavidin in *Escherichia coli* and allows expression of a streptavidin-Protein A chimeric protein. Another aspect of the current invention is the construction of an expression vector pTSAPA-2 for a streptavidin-Protein A chimeric protein by inserting the Protein A gene encoded in the plasmid pRIT11 into an expression vector for streptavidin-containing chimeric proteins pTSA-18F. Another aspect of the current invention is an amino acid composition of the streptavidin-Protein A chimeric protein encoded in pTSAPA-2. Another aspect of the current invention is the expression of gene fusion of streptavidin with Protein A using T7 expression system. Still another aspect of the current invention is a method of purification of the streptavidin-Protein A chimeric protein. Another aspect of the current invention is the method for conjugation of antibody-containing streptavidin-Protein A chimeric protein with various biological materials. Still another aspect of the current invention is an incorporation of the antibody-containing streptavidin-Protein A chimeric protein into biological materials containing biotin. Yet another aspect of the current invention is the method for introducing antibody materials into the tissue, removing the antibody from the tissue or labeling the tissue with antibody.

In some embodiments, the tetramers have 2, 3 or 4 different CDR-based peptidomimetics. In some embodiments, each monomer of the tetramer has a different CDR-based peptidomimetics. In some embodiments, the tetramer comprises two different CDR-based peptidomimetics.

The CDR-based peptidomimetics preferably comprise humanized sequences.

EXAMPLE

Introduction

AHNP is a peptidomimetic derived from the structure of a CDR-H3 loop of an anti-HER2 rhumAb 4D5. A chimeric DNA construct encoding AHNP fused to streptavidin was expressed in *E. coli* and purified as a recombinant fusion protein (ASA). Similar to streptavidin, the purified fusion protein formed a tetrameric structure and bound to biotin. Moreover, the fusion protein bound to Her2 and inhibited the proliferation of Her2-overexpressing cells as well as tumor growth induced by Her2-transformed cells. These data suggest that this fusion protein, ASA, while inheriting biophysical features from both AHNP peptide and streptavidin, can be used as an antibody-surrogate molecule in the diagnostics and treatment of Her2/neu-related tumors. Moreover, these studies establish a general principle by which monovalent peptidomimetics can become more functional by structured oligomerization.

Her2/neu (Neu, c-ErbB2) is a member of the epidermal growth factor receptor (EGFR) or HER family of tyrosine kinase receptors that also include HER1 (EGFR, c-erbB1), HER3 (c-erbB3), and HER4 (c-erbB4). Her2/neu is expressed on the surface of many breast and ovarian cancers, lung tumors as well as tumors of the pancreas. Extensive studies have shown Her2/neu plays a dominant role in mediating the malignant phenotype. The development of targeted therapy began with development of monoclonals to her2/neu. The anti-HER2 antibody "trastuzumab" (Herceptin; Genentech, San Francisco) has some effect in patients with advanced breast cancer overexpressing Her2 and has been approved by FDA to treat breast cancers. The antibody has been showed to antagonize the constitutive growth-signaling properties of the Her2 systems, enlist immune cells to attack and kill the tumor target, and augment chemotherapy-induced cytotoxicity.

There are some significant limitations to use of full-length antibody for tumor therapy. For example, the high cost for commercial production and the limited penetration to tumor cells are significant impediments. To overcome these problems, one solution is to use smaller antibody derived peptides. Recently, a HER2 binding peptidomemetics (shorted as BiP) AHNP (SEQ ID NO:1 FCDGFYACYMDV) was designed. AHNP was derived from the structure of the CDR-H3 loop of the anti-HER2 rhumAb 4D5, and demonstrated in vitro and in vivo activities of disabling HER2 tyrosine kinases similar to, but with far less affinity, than the monoclonal antibodies. These characteristics suggest potential for similar antibody-mimicking peptidomimetics to serve as reagents for tumor therapy.

The AHNP peptide was recombinantly fused to Streptavidin, a tetrameric protein produced by *Streptomyces avidinii* that binds to biotin with an extremely high affinity (Kd~$10^{-15}$ M). By doing so a Her2-binding multimeric BiP was created which has been named ASA. The streptavidin-biotin system has been adopted in many applications because of the strength of the interaction and the ease of biotinylation of both protein and DNA/RNA. ASA possesses the abilities to bind Her2 and to suppress the proliferation of Her2-transformed cells in vitro as well as in vivo. These studies serve as a principle to create new forms of antibody like molecules which are multivalent and built of a scaffold upon which relevant CDRs are disposed.

Experimental Protocol

Cell Line

T6-17 and NR6 cells were grown in DMEM medium supplemented with 10% heat inactivated fetal calf serum, L-glutamine (2 mM), penicillin (100 U/ml) and streptomycin (100 µg/ml) at 37° C. in a humidified 5% $CO_2$ atmosphere.

Construction of Plasmid

Two plasmids, pKMSH and pKMASH, were constructed to express Streptavidin and AHNP-Streptavidin fusion protein, respectively, under the control of T7 promoter and lacIq. The following primers were used to clone streptavidin or the fusion:

for Streptavidin,

```
primer19
                                          SEQ ID NO: 2
(5'AAAAAACATATGGAAGCAGGTATCACCGGCACACCTGGTACAACCAG CTCGGCTCGACCTTCATCGTGACCGCGGC-3')
and primer3-2dch
                                          SEQ ID NO: 3
(5'-AAGCTTTTATTAATGATGATGGTG-ATGATGG-3');
``` for AHNP fusion protein ASA,

```
primer1
                                          SEQ ID NO: 4
(5'AAAAAACATATGGTCGACTATTGCGATGGCTTTTATGCGTGCTATAT GGATGTGGGTGGTGGTGGTAG-3'),
and primer2
                                          SEQ ID NO: 5
(5'GGATGTGGGTGGTGGTGGTAGCAGATCTAACAGCAGCAGCGAAGCAG GTATCACCGGACAATGGTACAC-3')
and primer3-2dch.
                                          SEQ ID NO: 3
``` the amplified DNAs were ligated to pCR2.1 vector using a TA Cloning Kit (Invitrogen), digested with NdeI and HindIII, then respectively inserted: into the same restriction site of pET2.1 (a)+(Invitrogen).

Fusion Protein Production and Cyclization and Purification

*E. coli* BL21 Origami LysS (Novergen) harboring either pKMSH or pKMASH was grown with 50 µg/ml ampicillin at 0.25° C. When the OD at 600 nm reached 0.4, Streptavidin and ASA were induced to express with 0.5 mM isopropyl β-D-thiogalactopyranoside (IPTG) and cultured at 37° C. for 2.5 hr. These proteins were insoluble and existed in the inclusion body. After cells were sonicated, the pellet (inclusion body fraction) was obtained by centrifugation at 10,000×g for 30 min and then the pellet were solublized with 1q00 mM Tris-Cl (pH 7.5), containing 6M guanidine-HCl and 1 mM DTT at 10 mg/ml. A supernatant was obtained by centrifugation at 10,000×g for 30 min and then diluted against 20 times volume of 100 mM Tris-Cl (pH 7.5), containing 1 mM reduced form glutathion and 0.1 mM oxidized form glutathion. After dilution, A supernatant was obtained by centrifugation at 10,000×g for 30 min and then incubated for 45 min at 4° C. with 1 ml of Talon resin (CLONTECH), which has been equilibrated with buffer A comprising 100 mM Tris-Cl (pH 7.5) and 300 mM NaCl. The resin was packed into a column, and washed with 20 ml of buffer A and then 10 ml of buffer A supplemented with 30 mM imidazole. The Streptavidin or ASA was eluted with buffer A containing 250 mM imidazole. The fractions were dialyzed against PBS. Alternatively, insoluble fusion proteins were also solubilized by 8 M urea, purified through a Ni-NTA agarose column (Qiagen), and refolded by stepwise reduction of urea in the dialysis buffer.

Determination of Disulyide-bond Formation by Protein Alkylation with AMS

Disulfide-bond formation of ASA was determined. Alkylation of samples using the sulphydryl-specific reagent 4-acetamido-4'-maleimidylstilbene-2,2'-disulfonic acid (AMS; Molecular probes Inc.) was performed. After induction, four 100 µl aliquots of a single culture or four 100 µl aliquots containing the 2 µg of purified protein were prepared. Dithiothreitol (DTT) was added to two of these aliquots at 100 mM final concentrations (DTT-treated control samples), which were incubated for ten minutes at 100° C. All four aliquots were then precipitated with trichloroacetic acid (TCA, 10% W/V) for ten minutes at 4° C. The precipitated proteins were recovered by centrifugation at 10,000×g for 15 min and then washed once with 250 µl of ice cold aceton. Next, pellets were obtained by centrifugation at 10,000×g for 15 min and were air-dried and two of them, one previously treated DTT, were resuspended in 20 µl of an alkylating cocktail comprising 150 mM Tris-Cl (pH 7.5), 2% SDS (W/V) and 15 mM AMS. The other two pellets were resuspended in 20 µl of an alkylating cocktail lacking AMS. After 1 hr of incubation at room temperature, 20 µl of SDS-PAGE sample buffer (2×) lacking 2-mercaptoethanol were added to all samples, which were then analyzed by SDS-PAGE and immunoblotting with anti-streptavidin antibody conjugated HRP (Zymed Labratories).

MTT Assay

The MTT assay has been used modified method for measuring cell growth. T6-17 cells or NR6 cells were seeded in poly 2-hydroxyethyl methacrylate coated 96 well plates (50 µl/well, 800 cells/well or 1200 cells/well). Then the Streptavidin or ASA protein or the AHNP peptide were (50 µl/well, 0.69 µM or 6.9 µM) and incubate at 37° C. in a humidified 5% CO2 atmosphere for 48 hr. A total of 25 µl of MTT solution (5 mg/ml in PBS) was added to each well, and after 2 hr of incubation at 37° C., 100 µl of the extraction-buffer (20% w/v SDS, 50% N,N-dimethyl formamide, pH 4.7) were added. After an overnight incubation at 37° C., the optical density at 5700 nm was measured using an ELISA reader.

Enzyme-linked Immunosorbent Assays (ELISA)

The binding of ASA to Biotin and Her2 was determined by a modified ELISA assay. ELISA was performed at room temperature (RT) or 4° C. Purified streptavidin or ASA (0-1.1 µg/well) was immobilized on the biotin-coated ELISA plate (Pierce) for 1 hr at 4° C. in PBS. Excess protein was washed out and then purified Her2-human Fc fusion protein that was composed of the ectodomain of Her2 and the Fc of human IgG (originally from Xcyte Therapeutic, Seattle, Wash.) (50 ng/well) in PBS was added to each well and incubated at 4° C. After 3 hr incubation, plates were washed 6 times with PBS containing 0.1% Tween 20 (PBS-T; 150 µl/well) and anti-Her2 antibody was added in PBS (1:500 dilution; 50 µl/well). After 1 hr further incubation, plates were washed 6 times with PBS (200 µl/well) and anti-mouse IgG antibody conjugated HRP was added in PBS (1: 5000 dilution; 50 µl/well). Finally, plates were washed 6 times with PBS (200 µl/well) and bound anti-mouse IgG antibody-HRP was developed using an substrate solution (100 µl/well) containing 3,3',5,5'-tetramethylbenzene (1 tablet/10 ml solution; Sigma) in phosphate-citrate buffer (103 mM dibasic sodium phosphate, 24 mM citric acid, pH 5.0; Sigma). The reaction was allowed to proceed in the dark for 2 min at RT, and stopped with 2M $H_2SO_4$ (50 µl/well). The A450 nm value of the plates was determined using an ELISA reader. Bound streptavidin was detected by the same method using an anti-streptavidin-HRP in PBS (1; 500 dilution; 50 µL/well).

Mice

NCR homozygous athymic (nude) mice (six to eight weeks-old) were purchased from the National Cancer Institute. To induce tumor, $10^6$ transformed T6-17 cells were suspended in 100 µl of PBS and injected subcutaneously into the flank of each animal. Animals were maintained in accordance with guidelines of the Institutional Animal Care and Use Committee (IACUC) of the University of Pennsylvana. Tumor volume was calculated by the formula: π*length*width*Height/6.

Result and Discussion

Design of the AHNP Fusion Protein ASA

Figure 1:
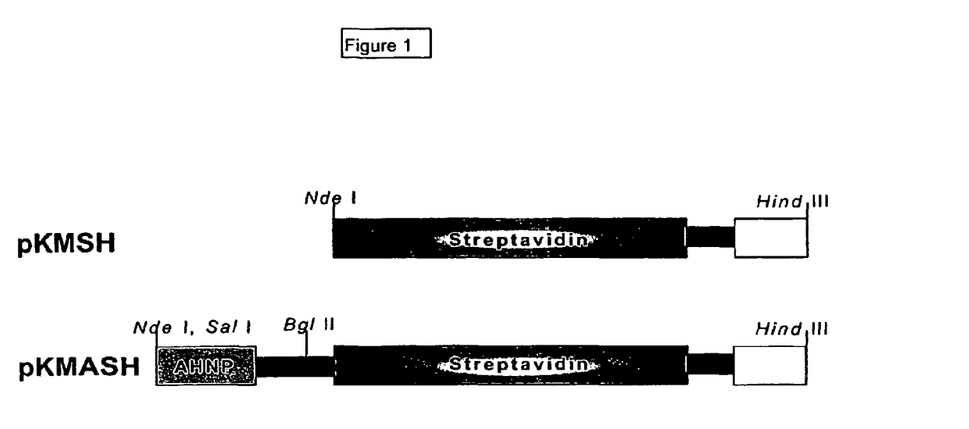
FIG. 1 shows an illustration of the construction of the expression vector of AHNP fusion protein (ASA) and the expression vector of streptavidin (SA).

Plasmid pKMSH was constructed by inserting the sequence encoding the core sequence of streptavidin into the NdeI and HindIII restriction site of pET21(a)+ (FIG. 1). pKMSH was then used as a platform for the construction of the AHNP-streptavidin fusion protein expression vector. The fusion protein ASA consists of 4 independent domains/units: 1) the AHNP peptide that binds to Her2; 2) a flexible 11 amino acid linker (SEQ ID NO:6 GGGGSRSNSSS) that may help to expose the AHNP peptide to the antigen; 3) the streptavidin core which forms a tetramer and can bind to biotin; and 4) a 4 amino acid linker (SEQ ID NO: 7 NSSS) and His-tag portion that was placed at the C terminus of the fusion protein to facilitate protein purification. To construct this fusion protein expression vector, two single-stranded oligonucleotides encoding the sequence of the AHNP and streptavidin was made as primers and then PCR product was inserted into the NdeI and HindIII restriction site of pET21 (a)+ (PKMASH; FIG. 1). Two restriction enzyme sites (Sal I and Bgl II were engineered at the N-terminal of AHNP and inside the linker, respectively, for the convenience of replacing the AHNP sequence in the future.

The N-terminus of streptavidin is exposed on the surface of proteins. Thus, the AHNP portion should stay on the surface of the tetramer and be accessible to the antigen (Her2 protein). Since streptavidin has no internal cysteines, the disulfide bond that is designed to constrain AHNP should not be disturbed. These ideal characteristics of streptavidin may facilitate to design functional peptide-fusion proteins mimicking antibody.

Expression and Purification of the ASA in E. coli

Figure 2:
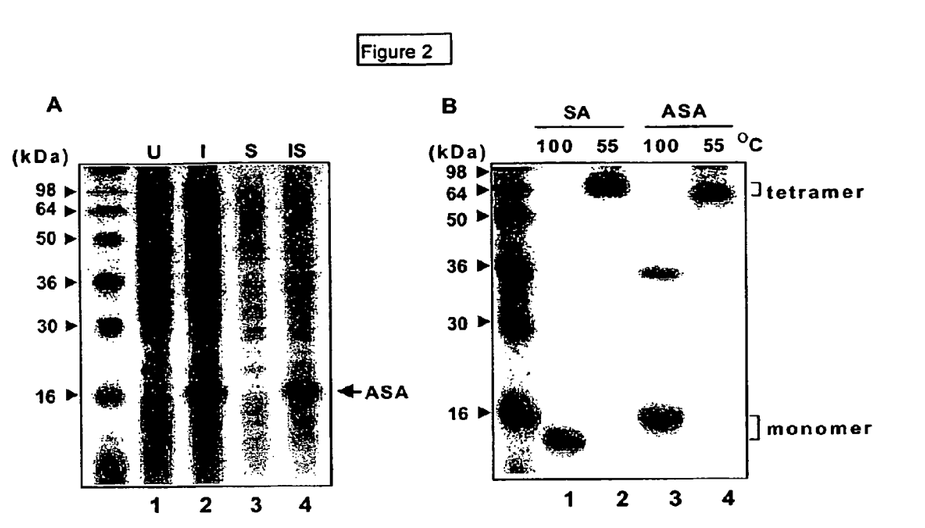
FIG. 2, panels A and B show data from expression and purification of fusion protein ASA and streptavidin. (Panel A) Induction of ASA expression by IPTG. Arrow shows the position of expressed ASA. Lane 1, total protein of uninduced cells (U); Lane 2, total protein of induced cells (I); Lane 3, soluble fraction of induced cells (S); Lane 4, insoluble fraction of induced cells (IS). (Panel B) Purified ASA and streptavidin by CO2+ column. Lanes 1 and 3, purified proteins were heated for 5 min in boiling water in the presence of Sodium Dodecyl Sulfate (SDS), Dithiothreitol (DTT) and 2-Mercaptoethanol (2-ME); Lanes 2 and 4, samples were heated for 5 min at 55° C. in the presence of SDS and DTT without 2-ME. Lanes 1 and 2, Streptavidin: Lanes 3 and 4, ASA.

Periplasmic expression of ASA and SA was tried but these proteins formed insoluble inclusion bodies even in the periplasmic fraction with resultant very low yield. Alternatively, E. coli BL21 strain (origami pLysS) was transformed with pKMSH or pKMASH to express the recombinant protein in the cytoplasm. On SDS-PAGE analysis of, total bacterial cell lysates, proteins were expressed efficiently (lane 2; FIG. 2, Panel, A). While SA was expressed as a soluble protein, ASA was insoluble and formed inclusion bodies (lane 4; FIG. 2, Panel A). Insoluble ASA fractions were isolated from cell lysates and dissolved in Gdn-HCl under the conditions where any disulfide bonds are reduced to sulfhydryl groups. The resulting solutions was diluted with the 20 times volume of the refolding solution to allow the expressed protein to refold and form the disulfide bond correctly. Refolded proteins were purified by $CO^{2+}$ resin under oxidative condition, where the AHNP peptide should be in an oxidated circular form. In this purification procedure, the protein yield was extremely low (1 mg/10 L cultured cell), because the most of all protein was precipitated during the refolding step. It was reported that the use of high protein concentration in the streptavidin fusion protein refolding step caused the formation of the inter-molecular disulfide bond and led to precipitation. Thus, use of lower protein concentration in the refolding step may be helpful to improve final yield. After purification, SDS-PAGE of both streptavidin and ASA showed a single band of ~16 kDa (lane 1, 3; FIG. 2, Panel B) when the protein was heated at 100° C. in the presence of SDS. Under these conditions streptavidin dissociates into subunits. ASA was observed at a higher position than streptavidin, because of the additional AHNP, His tag and linker sequences. Under milder conditions (55° C.), streptavidin and ASA appeared on the SDS-PAGE as a single band at a higher position of ~64 kDa (lane 2, 4; FIG. 2, Panel B), indicating that these proteins form tetramers.

Figure 3:
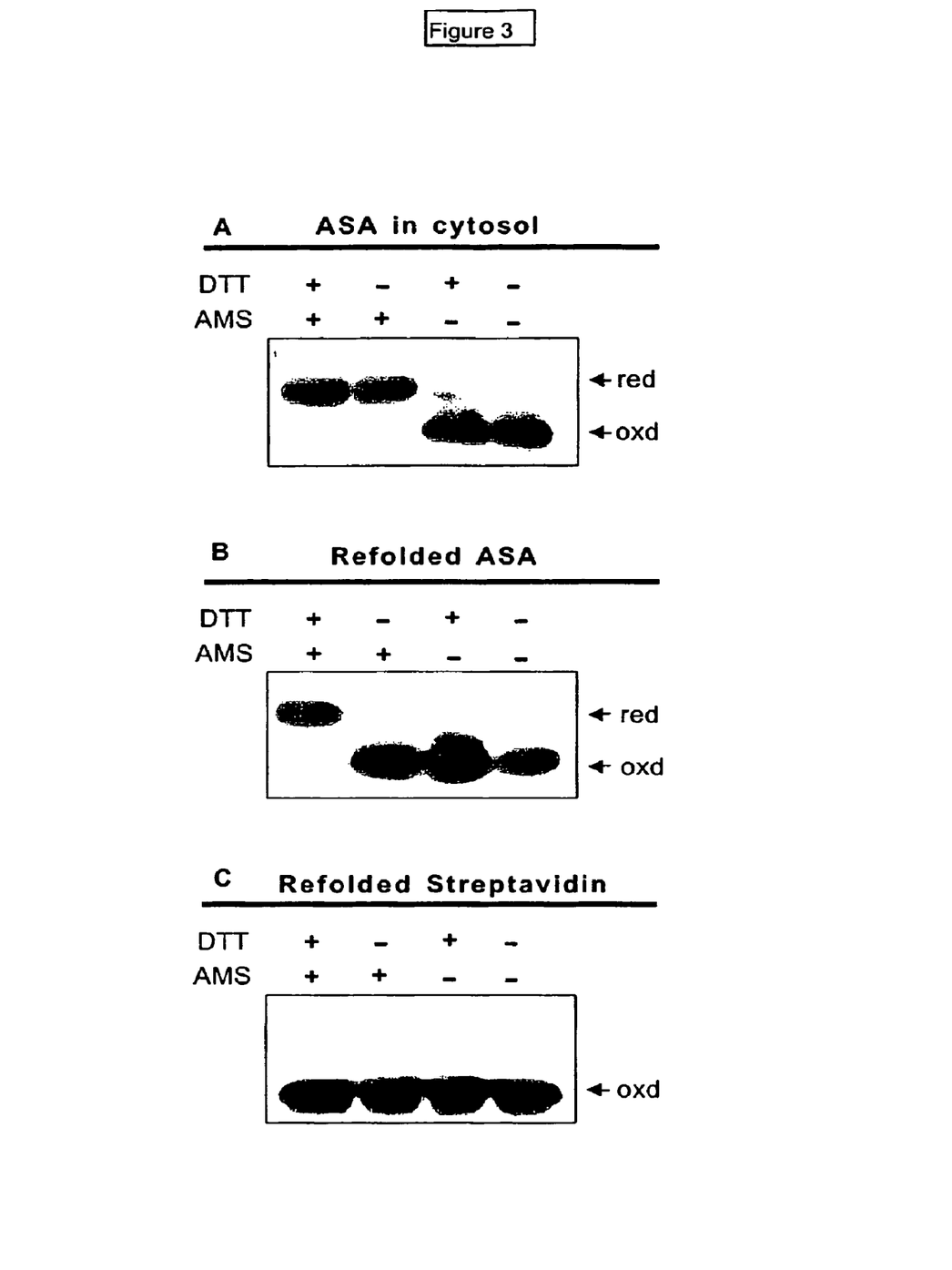
FIG. 3, panels A, B and C are data showing disulfide bond formation in the ASA fusion protein and streptavidin. AMS-alkylation was used to study if disulfide bonds were formed in ASA produced in the cytoplasm of E.coli BL21 LysE (Panel A) and after refolding (Panel B). Same method was also used to study refolded streptavidin. The alkylated and non-alkylated form were separated by their different mobility in non-reducing Sodium Dodecyl Sulfate-Polyacrylamide Gel Electrophoresis (SDS-PAGE) and visualized by Western blot probed with anti-streptavidin antibody.

In ASA, a disulfide bond was designed between the two cysteines in the AHNP sequence. Formation of disulfide bonds is important for correct protein folding to obtain biological activity. In antibody-derived proteins, disulfide bonds play a critical role in maintaining the structural frame work required for binding to antigens. Disulfide bond formation is essential to constrain the mimetic peptides. The sulphydryl-alkylating reagent 4-acetamide-4'-maleimidylatylbene-2,2'-disulfonic acid (AMS, Mr ~500 Da) was chosen to study if the fusion proteins-form the required disulfide bond. AMS covalently binds to free thiol groups in reduced proteins, increasing their molecular mass and preventing any further oxidation. After AMS incubation, the reduced and oxidized forms of a given polypeptide can be separated by non-reducing SDS-PAGE with the reduced form moving to a higher molecular weight position). As shown in FIG. 3, raw ASA that was expressed in bacteria was reduced and bound to AMS independent of the DTT treatment. This was not unexpected since the reducing environment of the E. coli cytoplasm is well known. However, AMS bound to purified ASA fusion proteins only if it was pre-treated with dithiotreitol (DTT). The data suggest that the purification procedure was able to facilitate the disulfide bond formation in the protein. Since streptavidin has no cysteine, AMS did to affect the mobility of streptavidin on the SDS-PAGE (FIG. 3, Panel C).

Binding Analysis of ASA

Figure 4:
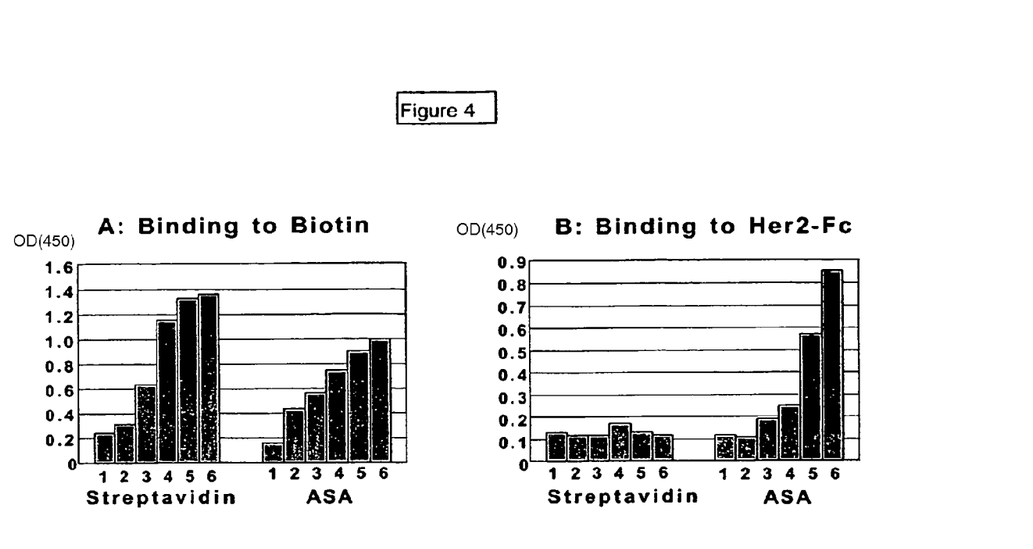
FIG. 4, panels A and B show data from enzyme-linked immunosorbent assay (ELISA) analysis of recombinant proteins for biotin and Her2-Fc binding ability. Panel A: Streptavidin or ASA was immobilized on biotin-coated plate. Bound protein was detected using an anti-streptavidin antibody-HRP. Panel B: After immobilization of Streptavidin or ASA on biotin-coated plate, Her2-human Fc fusion was added to each plate and bound fusion protein was detected using anti-Her2 antibody and anti-mouse IgG-HRP. The amounts of Streptavidin or ASA fusion protein used in this experiment were: well 1: 0; 2: 0.11 ng; 3: 1.1 ng; 4: 11 ng; 5: 110 ng; 6: 1100 ng.

The ASA fusion protein was tested to determine if it would bind to biotin as well as Her2. To test their ability to bind biotin, streptavidin and ASA were added to biotin-coated ELISA plate wells and the HRP-conjugated anti-streptavidin antibody was used as the detection antibody in an ELISA. Both streptavidin and ASA bound to biotin in a dose-dependent manner (FIG. 4, Panel A). ASA and streptavidin were next coated to biotin-coated ELISA plate followed by incubation with Her2-Fc. Bound Her2-Fc was detected by the mouse anti-Her2 antibody (4D5) and the HRP-conjugated anti-mouse IgG antibody. ASA was able to bind to the Her2-Fc fusion in a dose-dependent manner, while streptavidin didn't bind to the Her2-human Fc fusion protein even at the highest concentration (FIG. 4, Panel B). These data suggested the ASA retains the activity to bind both Her2 and biotin.

Biological Activity of the ASA

Figure 5:
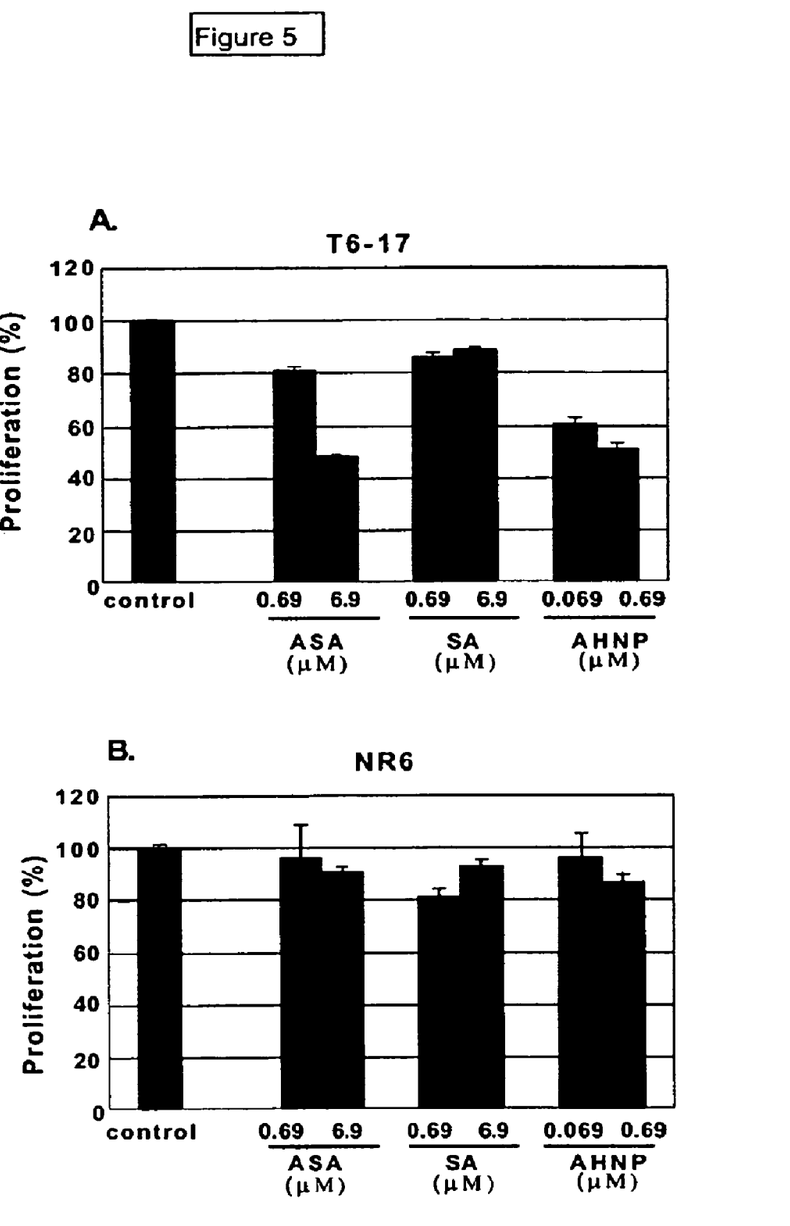
FIG. 5, panels A and B show inhibition of cell proliferation by ASA. Effects of ASA treatment, or treatments with streptavidin and the peptide AHNP, on the proliferation of T6-17 (Her2 transformed cells, Panel A) or NR6 (control cells, Panel B) were shown; Cell proliferation was measured by the standard MTT assay performed on poly-HEMA plates (for T6-17) or regular tissue culture plates (for NR6).

Next, the AHNP fusion ASA was analyzed to determine if it could inhibit proliferation of Her2/neu-transformed cells as judged by the MTT assay for mitochondrial viability. In the T6-17 cell line which overexpresses Her2 receptors, treatment with ASA fusion proteins at two different concentrations resulted in 20-50% inhibition of cell proliferation in a dose dependent manner (FIG. 5, Panel A). Inhibitory effects were not observed in the control. NR6 cell line (FIG. 5, Panel B). Another AHNP fusion protein that with a 22 amino acid linker showed almost no specific growth inhibitory effect to these two cell lines, in a comparable manner to the streptavidin control. These data suggest that the ASA fusion protein specifically inhibits the proliferation of Her2-overexpressing cells and its activity may be affected by linker size. However, about 10 times more of ASA, in molar concentration than the AHNP peptide, was necessary to achieve 50% cell growth inhibition in vitro.

In Vivo Activity

Figure 6:
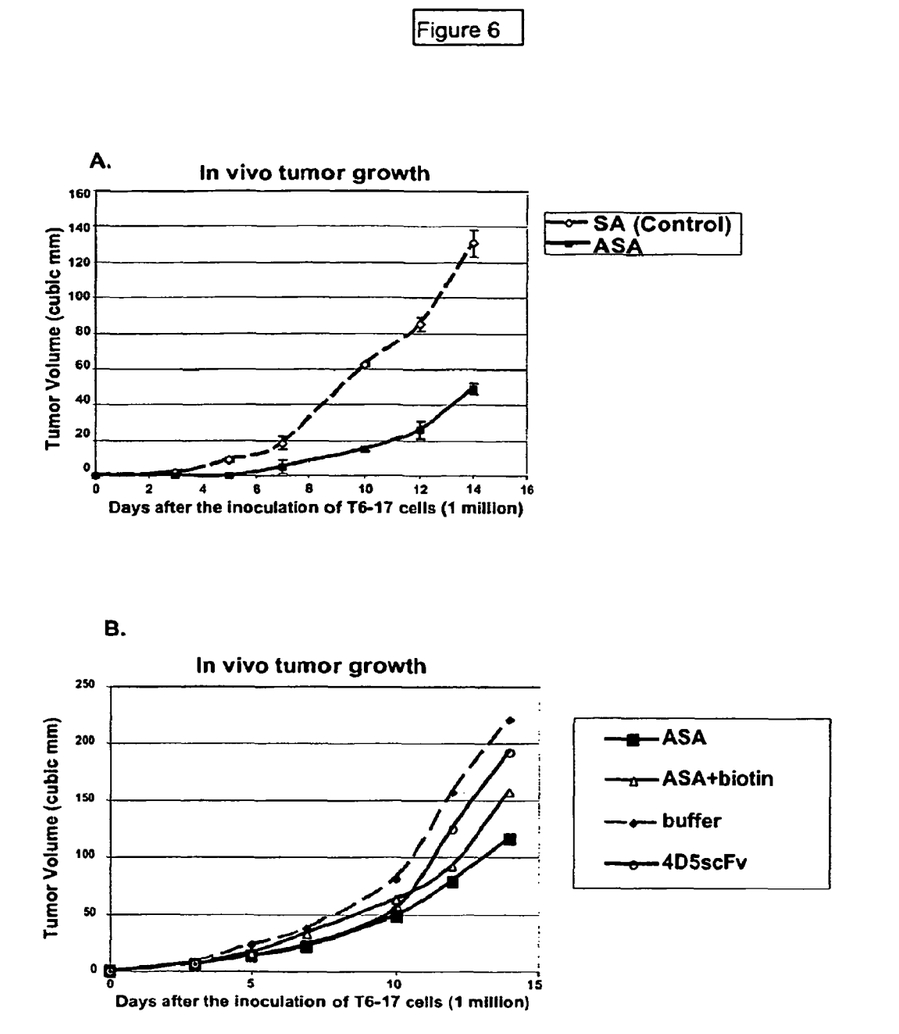
FIG. 6, panels A and B show inhibition of tumor growth by ASA. 1 million of T6-17 cells were injected subcutaneously into nude mice to induce the tumor growth. Panel A. Treatment of ASA started from day 0. Panel B. Treatment started on day 2 after tumor were palpable.

T6-17 cells were transformed by the over-expression of human Her2/neu (ref). After introduced to nude mice subcutaneously, palpable tumors appear about 48-72 hours later. In one experiment, animals were treated with either streptavidin or ASA (11.25 mg/kg/week). Treatment stared from day 0 and was provided to animals by three subcutaneous injections each week. Treatment with ASA prevented the appearance of palpable tumor until day 7 and reduced the tumor size by 62% at day 14 (FIG. 6 Panel A). Treatment was also provided to mice by a different administration route in a second experiment, in which intraperitoneal treatment started day 2 after palpable tumor appeared (~2 cubic mm) (FIG. 6, Panel B). ASA was given at the dose of 15 mg/kg/week, divided into three injections. Again, at day 14 we observed about 47.6% reduction of tumor size in the ASA group compared with vehicle control group. Interestingly, the biotin-bound form of ASA showed a reduced effect in the inhibition of tumor growth in a parallel experiment (28.8% reduction in tumor size at day 14). Unexpectedly, treatment with 4D5scFv did not reveal significant suppression of tumor-growth-after day 10.

Discussion the CDR approach to create antibody mimetic molecules by constraining the CDR regions from antibodies was established previously. The CDR peptide is much smaller than the antibody but retains binding affinity to the antigen as well as biological activity as the antibody. However, peptides have generally a very short in vivo half-life (about 2 hours) and the rapid clearance from circulation sometimes limits their use as pharmaceuticals.

As a practical approach to improve the binding of low affinity ligand, multimerization has been pursued by many laboratories. A pentameric scaffold was previously explored for Her2-binding peptides from phage libraries. In accordance with the present invention a functional tetrameric peptide fusion protein ASA was designed and is described herein. This protein, after being successfully synthesized and purified from E. coli expression system, bound to both Her2 and biotin and inhibited cell proliferation of Her2 expressed cells.

Streptavidin was chosen as a tetrameric scaffold for AHNP for several reasons. Firstly, streptavidin fusion has been constructed successfully for other functional cyclic peptides. Secondly, with high affinity to bind biotin, the fusion protein will be able to carry biotinylated therapeutics (such as cytotoxins) or labeling reagents to tumor cells with Her2 expression. Such a strategy has been tested on antibody-streptavidin conjugates but the results are varied because the big size of antibody. In addition, the fusion can also be used to replace antibodies in assays utilizing the biotin-streptavidin systems. Thirdly, the in vivo pharmacokinetics of streptavidin has been well studies: even in patient. Streptavidin by itself showed a serum half-life of about 12 hours, an improved; clearance than the AHNP peptide.

The AHNP-streptavidin fusion construct ASA, which forms a tetramer after recombinantly expressed and refolded, did demonstrate higher affinity for Her2 (ASA: AHNP=35 nM (monomer): 350 nM). Although ASA demonstrated lower proliferation inhibition activity than the AHNP peptide in vitro, it did reach comparable activity as AHNP of ~30 fold molar excess in reducing the tumor growth in vivo.

The biotin-binding capability of ASA appears to affect its in vivo activity to suppress tumor. As a essential vitamin, biotin functions as co-enzymes for several carboxylases and decarboxylases (e.g. pyruvate carboxylase, acetyl CoA carboxylase, etc.) that are critical for the metabolism of cells, particularly the synthesis of fatty acids and gluconeogenesis. It is reported that tumor cells consume more biotin than normal cells. Accumulation of biotin around or in tumors has also been suggested to localize to tumors after it was administrated to patients with squamous cell carcinoma.

ASA may interfere with biotin-required metabolism by binding to biotin and sequester it from being utilized. Fatty acid synthase, a critical enzyme in fatty acid synthesis that biotin is involved, has been reported with elevated expression in many types of cancer cells (breast, colorectal, ovarian, endometrial and prostatic cancers). In human breast cancer cells, an inhibitor to fatty acid synthase was reported to induce apoptosis, an event proceeded by fatty acid synthesis inhibition and DNA synthesis inhibition.

In summary, a protein engineering approach to tetramerize the functional anti-Her2 peptide is described. Since ASA can bind to biotin, it may carry biotinylated therapeutics, such as toxin or heavy metals, to enhance its in vivo activity. In addition to using this recombinant fusion protein therapeutically, ASA may be used as the tumor imaging reagent to replace antibodies. In the most successful two-step tumor imaging procedure, the antibody has to be linked to streptavidin first before it can be used in a pre-target step. ASA, with full biotin-binding activity of streptavidin, is completely compatible with such a two-step system.

```
SEQ ID NO: 8 ASA
MET VAL ASP PHE CYS ASP GLY PHE TYR ALA CYS TYR
MET ASP VAL GLY GLY GLY GLY SER ARG SER ASN SER
SER SER GLU ALA GLY ILE THR GLY THR TRP TYR ASN
GLN LEU GLY SER THR PHE ILE VAL THR ALA GLY ALA
ASP GLY ALA LEU THR GLY THR TYR GLU SER ALA VAL
GLY ASN ALA GLU SER ARG TYR VAL LEU THR GLY ARG
TYR ASP SER ALA PRO ALA THR ASP GLY SER GLY THR
ALA LEU GLY TRP THR VAL ALA TRP LYS ASN ASN TYR
ARG ASN ALA HIS SER ALA THR THR TRP SER GLY GLN
TYR VAL GLY GLY ALA GLU ALA ARG ILE ASN THR GLN
TRP LEU LEU THR SER GLY THR THR GLU ALA ASN ALA
TRP LYS SER THR LEU VAL GLY HIS ASP THR PHE THR
LYS VAL LYS PRO SER ALA ALA SER ASN SER SER SER
HIS HIS HIS HIS HIS HIS

SEQ ID NO: 9 FULL LENGTH STREPTAVIDIN
MET ARG LYS ILE VAL VAL ALA ALA ILE ALA VAL SER
LEU THR THR VAL SER ILE THR ALA SER ALA SER ALA
ASP PRO SER LYS ASP SER LYS ALA GLN VAL SER ALA
ALA GLU ALA GLY ILE THR GLY THR TRP TYR ASN GLN
LEU GLY SER THR PHE ILE VAL THR ALA GLY ALA ASP
GLY ALA LEU THR GLY THR TYR GLU SER ALA VAL GLY
ASN ALA GLU SER ARG TYR VAL LEU THR GLY ARG TYR
ASP SER ALA PRO ALA THR ASP GLY SER GLY THR ALA
LEU GLY TRP THR VAL ALA TRP LYS ASN ASN TYR ARG
ASN ALA HIS SER ALA THR THR TRP SER GLY GLN TYR
VAL GLY GLY ALA GLU ALA ARG ILE ASN THR GLN TRP
LEU LEU THR SER GLY THR THR GLU ALA ASN ALA TRP
LYS SER THR LEU VAL GLY HIS ASP THR PHE THR LYS
VAL LYS PRO SER ALA ALA SER ILE ASP ALA ALA LYS
LYS ALA GLY VAL ASN ASN GLY ASN PRO LEU ASP ALA
VAL GLN GLN

SEQ ID NO: 1 AHNP
PHE CYS ASP GLY PHE TYR ALA CYS TYR MET ASP VAL

SEQ ID NO: 10 AHNPY
TYR CYS ASP GLY PHE TYR ALA CYS TYR MET ASP VAL

SEQ ID NO: 6 LINKER SEQUENCE
GLY GLY GLY GLY SER ARG SER ASN SER SER SER
```

What is claimed is:

1. A purified recombinant fusion protein comprising a binding peptidomimetic and a biotin-binding streptavidin core sequence, wherein said binding peptidomimetic comprises a binding domain of a heterologous polypeptide derived from the CDR-H3 loop of an anti-HER2 rhumA 4D5 and wherein said binding peptidomimetic is fused to the N-terminus of a streptavidin core sequence by a flexible linker; said fusion protein comprising SEQ ID NO:8.

* * * * *

SEQUENCE LISTING

<160> NUMBER OF SEQ ID NOS: 10

<210> SEQ ID NO 1
<211> LENGTH: 12
<212> TYPE: PRT
<213> ORGANISM: Artificial Sequence -continued

```
<220> FEATURE:
<223> OTHER INFORMATION: ANHP peptidomemetic

<400> SEQUENCE: 1

Phe Cys Asp Gly Phe Tyr Ala Cys Tyr Met Asp Val
1               5                   10

<210> SEQ ID NO 2
<211> LENGTH: 76
<212> TYPE: DNA
<213> ORGANISM: Artificial Sequence
<220> FEATURE:
<223> OTHER INFORMATION: Streptavidin primer 19

<400> SEQUENCE: 2
aaaaaacata tggaagcagg tatcaccggc acacctggta caaccagctc ggctcgacct      60
tcatcgtgac cgcggc                                                      76

<210> SEQ ID NO 3
<211> LENGTH: 31
<212> TYPE: DNA
<213> ORGANISM: Artificial Sequence
<220> FEATURE:
<223> OTHER INFORMATION: Streptavidin primer 3-2dch

<400> SEQUENCE: 3
aagcttttat taatgatgat ggtgatgatg g                                     31

<210> SEQ ID NO 4
<211> LENGTH: 68
<212> TYPE: DNA
<213> ORGANISM: Artificial Sequence
<220> FEATURE:
<223> OTHER INFORMATION: AHNP fusion primer 1

<400> SEQUENCE: 4
aaaaaacata tggtcgacta ttgcgatggc ttttatgcgt gctatatgga tgtgggtggt      60
ggtggtag                                                               68

<210> SEQ ID NO 5
<211> LENGTH: 69
<212> TYPE: DNA
<213> ORGANISM: Artificial Sequence
<220> FEATURE:
<223> OTHER INFORMATION: ANHP fusion primer 2

<400> SEQUENCE: 5
ggatgtgggt ggtggtggta gcagatctaa cagcagcagc gaagcaggta tcaccggaca      60
atggtacac                                                              69

<210> SEQ ID NO 6
<211> LENGTH: 11
<212> TYPE: PRT
<213> ORGANISM: Artificial Sequence
<220> FEATURE:
<223> OTHER INFORMATION: Flexible Amino Acid Linker

<400> SEQUENCE: 6

Gly Gly Gly Gly Ser Arg Ser Asn Ser Ser Ser
1               5                   10

<210> SEQ ID NO 7
<211> LENGTH: 4
<212> TYPE: PRT
<213> ORGANISM: Artificial Sequence
```

<220> FEATURE:
<223> OTHER INFORMATION: Histidine tag linker

<400> SEQUENCE: 7

Asn Ser Ser Ser
1

<210> SEQ ID NO 8
<211> LENGTH: 162
<212> TYPE: PRT
<213> ORGANISM: Artificial Sequence
<220> FEATURE:
<223> OTHER INFORMATION: ASA fusion protein sequence

<400> SEQUENCE: 8

Met Val Asp Phe Cys Asp Gly Phe Tyr Ala Cys Tyr Met Asp Val Gly
1               5                   10                  15

Gly Gly Gly Ser Arg Ser Asn Ser Ser Glu Ala Gly Ile Thr Gly
            20                  25                  30

Thr Trp Tyr Asn Gln Leu Gly Ser Thr Phe Ile Val Thr Ala Gly Ala
        35                  40                  45

Asp Gly Ala Leu Thr Gly Thr Tyr Glu Ser Ala Val Gly Asn Ala Glu
    50                  55                  60

Ser Arg Tyr Val Leu Thr Gly Arg Tyr Asp Ser Ala Pro Ala Thr Asp
65                  70                  75                  80

Gly Ser Gly Thr Ala Leu Gly Trp Thr Val Ala Trp Lys Asn Asn Tyr
                85                  90                  95

Arg Asn Ala His Ser Ala Thr Thr Trp Ser Gly Gln Tyr Val Gly Gly
            100                 105                 110

Ala Glu Ala Arg Ile Asn Thr Gln Trp Leu Leu Thr Ser Gly Thr Thr
        115                 120                 125

Glu Ala Asn Ala Trp Lys Ser Thr Leu Val Gly His Asp Thr Phe Thr
    130                 135                 140

Lys Val Lys Pro Ser Ala Ala Ser Asn Ser Ser Ser His His His His
145                 150                 155                 160

His His

<210> SEQ ID NO 9
<211> LENGTH: 183
<212> TYPE: PRT
<213> ORGANISM: Artificial Sequence
<220> FEATURE:
<223> OTHER INFORMATION: Streptavidin protein sequence

<400> SEQUENCE: 9

Met Arg Lys Ile Val Val Ala Ala Ile Ala Val Ser Leu Thr Thr Val
1               5                   10                  15

Ser Ile Thr Ala Ser Ala Ser Ala Asp Pro Ser Lys Asp Ser Lys Ala
            20                  25                  30

Gln Val Ser Ala Ala Glu Ala Gly Ile Thr Gly Thr Trp Tyr Asn Gln
        35                  40                  45

Leu Gly Ser Thr Phe Ile Val Thr Ala Gly Ala Asp Gly Ala Leu Thr
    50                  55                  60

Gly Thr Tyr Glu Ser Ala Val Gly Asn Ala Glu Ser Arg Tyr Val Leu
65                  70                  75                  80

Thr Gly Arg Tyr Asp Ser Ala Pro Ala Thr Asp Gly Ser Gly Thr Ala
                85                  90                  95

Leu Gly Trp Thr Val Ala Trp Lys Asn Asn Tyr Arg Asn Ala His Ser
            100                 105                 110

```
Ala Thr Thr Trp Ser Gly Gln Tyr Val Gly Gly Ala Glu Ala Arg Ile
            115                 120                 125

Asn Thr Gln Trp Leu Leu Thr Ser Gly Thr Thr Glu Ala Asn Ala Trp
        130                 135                 140

Lys Ser Thr Leu Val Gly His Asp Thr Phe Thr Lys Val Lys Pro Ser
145                 150                 155                 160

Ala Ala Ser Ile Asp Ala Ala Lys Lys Ala Gly Val Asn Asn Gly Asn
                165                 170                 175

Pro Leu Asp Ala Val Gln Gln
            180

<210> SEQ ID NO 10
<211> LENGTH: 12
<212> TYPE: PRT
<213> ORGANISM: Artificial Sequence
<220> FEATURE:
<223> OTHER INFORMATION: AHNPY peptidomemetic sequence

<400> SEQUENCE: 10

Tyr Cys Asp Gly Phe Tyr Ala Cys Tyr Met Asp Val
1               5                   10
```